(12) United States Patent
Baker et al.

(10) Patent No.: US 8,398,678 B2
(45) Date of Patent: Mar. 19, 2013

(54) HALLUX VALGUS REPAIRS USING SUTURE-BUTTON CONSTRUCT

(75) Inventors: Christian M. Baker, Weymouth, MA (US); Christopher P. Chiodo, Walpole, MA (US)

(73) Assignees: Arthrex, Inc., Naples, FL (US); The Brigham and Women's Hospital, Inc., Boston, MA (US)

( * ) Notice: Subject to any disclaimer, the term of this patent is extended or adjusted under 35 U.S.C. 154(b) by 172 days.

(21) Appl. No.: 13/033,236

(22) Filed: Feb. 23, 2011

(65) Prior Publication Data

US 2011/0224729 A1  Sep. 15, 2011

Related U.S. Application Data

(60) Provisional application No. 61/314,015, filed on Mar. 15, 2010.

(51) Int. Cl.
*A61B 17/88* (2006.01)
*A61B 17/06* (2006.01)

(52) U.S. Cl. .......... 606/213; 606/60; 606/300; 623/908; 128/898

(58) Field of Classification Search .................. 606/232, 606/300, 60; 623/908; 128/898
See application file for complete search history.

(56) References Cited

U.S. PATENT DOCUMENTS

| | | | |
|---|---|---|---|
| 4,159,716 A | 7/1979 | Borchers | |
| 4,409,974 A | 10/1983 | Freedland | |
| 5,306,301 A | 4/1994 | Graf et al. | |
| 5,529,075 A * | 6/1996 | Clark ........................ | 128/898 |
| 5,888,203 A | 3/1999 | Goldberg | |
| 6,391,031 B1 | 5/2002 | Toomey | |
| 6,719,801 B1 | 4/2004 | Holt | |
| 6,964,645 B1 | 11/2005 | Smits | |
| 7,235,091 B2 | 6/2007 | Thornes | |
| 7,875,058 B2 | 1/2011 | Holmes, Jr. | |
| 2003/0023268 A1 | 1/2003 | Lizardi | |
| 2003/0236555 A1 | 12/2003 | Thornes | |
| 2006/0178702 A1 | 8/2006 | Pierce et al. | |
| 2006/0264961 A1 | 11/2006 | Murray-Brown | |
| 2007/0010818 A1 | 1/2007 | Stone et al. | |
| 2008/0177302 A1 | 7/2008 | Shurnas | |
| 2008/0208252 A1 * | 8/2008 | Holmes ........................ | 606/232 |
| 2008/0269743 A1 | 10/2008 | McNamara et al. | |

(Continued)

FOREIGN PATENT DOCUMENTS

WO WO 2009/018527 A1 2/2009

*Primary Examiner* — Darwin Erezo
*Assistant Examiner* — Shaun L David
(74) *Attorney, Agent, or Firm* — Dickstein Shapiro LLP

(57) ABSTRACT

A technique and associated instrumentation for correcting large intermetatarsal angles that result from hallux valgus. The system includes a button and a suture loop attached to the button. A suture strand is threaded through holes in the button to attach the button to the suture. The suture ends are then brought together (by being swaged, spliced or cinched together, for example) to form the suture loop comprising a continuous, uninterrupted suture loop with a single strand of swaged-together ends. The swaged-together ends may be attached to a suture passing instrument such as a K-wire (Kirschner wire) that may be further used to drill a hole through the first and second metatarsals. The swaged-together ends of the suture are then passed through the drill holes in the first and second metatarsals; and the ends of the suture are pulled until the button abuts the second metatarsal. The swaged together portion of the suture loop is then cut, and the free suture ends are passed through holes in another (second) button. The suture ends are pulled to adjust the first metatarsal to a correct intermetatarsal angle, and the first metatarsal is secured in place by tying the ends of the suture together against the second button.

6 Claims, 7 Drawing Sheets

U.S. PATENT DOCUMENTS

| | | |
|---|---|---|
| 2008/0281355 A1 | 11/2008 | Mayer et al. |
| 2009/0036893 A1 | 2/2009 | Kartalian et al. |
| 2010/0076504 A1 | 3/2010 | McNamara et al. |
| 2010/0152752 A1 | 6/2010 | Denove et al. |
| 2010/0211071 A1* | 8/2010 | Lettmann et al. ............... 606/60 |
| 2010/0268273 A1 | 10/2010 | Albertorio et al. |
| 2011/0118780 A1 | 5/2011 | Holmes, Jr. |

* cited by examiner

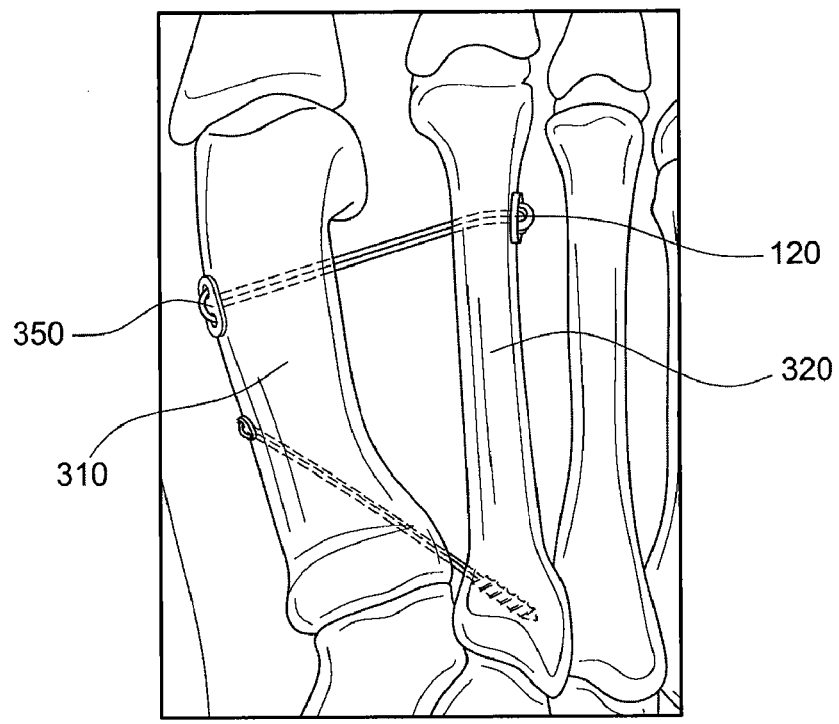
FIG. 11
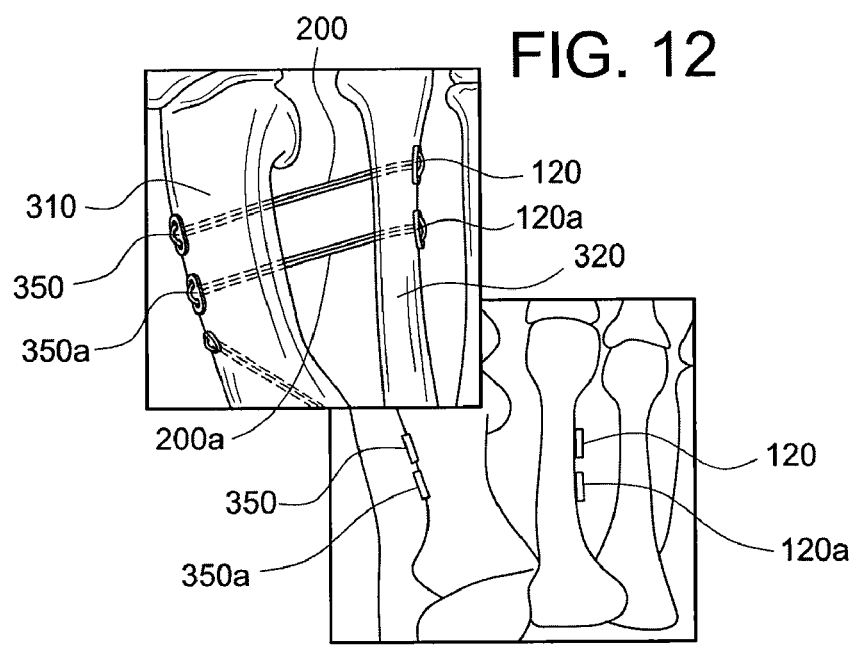
FIG. 12
FIG. 12(a)

HALLUX VALGUS REPAIRS USING SUTURE-BUTTON CONSTRUCT

CROSS-REFERENCE TO RELATED APPLICATIONS

This application claims the benefit of U.S. Provisional Application No. 61/314,015, filed Mar. 15, 2010, the entire disclosure of which is incorporated by reference herein.

FIELD OF THE INVENTION

The present invention relates to the field of surgery and, in particular, to a bunion repair technique using a suture-button construct and to a device.

BACKGROUND OF THE INVENTION

Hallux valgus, more commonly known as bunions, is a condition where the first metatarsal deviates inward toward the second metatarsal. This results in an intermetatarsal angle that is too large. Bunions are caused when certain tendons, ligaments, and supportive structures of the first metatarsal no longer function correctly causing the first metatarsal to be misaligned. Bunions may be caused by a variety of conditions intrinsic to the structure of the foot, such as flat feet, excessive ligamentous flexibility, abnormal bone structure, and certain neurological conditions.

Bunions are commonly associated with arthritis of the first metatarsal, diminished and/or altered range of motion and discomfort when pressure is applied to the first metatarsal or with motion of the joint. Treatments of bunions vary and, depending on severity of the misalignment, can range from rest, medication, orthotics and, in extreme cases, surgery.

Numerous techniques have been used during surgery to correct the intermetatarsal angle, including the reshaping or removal of part of the first metatarsal bone. Other techniques have also been used to reduce the intermetatarsal angle to a normal angle of less than 9° to 11°. One way to reduce the intermetatarsal angle is by connecting the first and second metatarsals together with a suture, to secure the first metatarsal at a proper angle.

One such technique for hallux valgus repairs employs a suture-button construct as detailed in U.S. Patent Publ. No. 2008/0208252 (filed on Jan. 17, 2008 and assigned to Arthrex, Inc.). According to U.S. Patent Publ. No. 2008/0208252, a suture strand is double looped through first and second buttons, and a pull-through suture is attached to one of the buttons and to a needle. This technique requires one large diameter hole, drilled through both the first and second metatarsals, to allow passage of the button.

Another technique employs a deconstructed suture-button construct sold by Arthrex, Inc. of Naples, Fla. under the tradename Mini TightRope®. The deconstructed Mini Tight-Rope® technique involves drilling two small drill holes through the first and second metatarsal, and passing sutures through each hole, thereby connecting the first and second metatarsals. This procedure requires a higher degree of technical difficulty, however, since both drill holes must be parallel and in the same plane. What is needed is a simpler technique but with equivalent strength. Also needed is a technique that requires only one small hole in lieu of multiple holes drilled through the first and second metatarsals.

BRIEF SUMMARY OF THE INVENTION

The present invention provides systems and methods for correcting large intermetatarsal angles that result from hallux valgus. The system includes a button and a suture loop attached to the button. According to an exemplary embodiment, a suture strand is woven through holes in the button to attach the button to the suture. The suture ends are then brought together (by being swaged, spliced or cinched together, for example) to form the suture loop comprising a continuous, uninterrupted suture loop and a single strand of swaged-together ends attached to the loop. The swaged-together ends may be attached to a suture passing instrument such as a K-wire (Kirschner wire) that may be further used to drill the hole.

A method for correcting intermetatarsal angles that result from hallux valgus employing the suture-button construct of the present invention (with a continuous suture loop attached to a button) includes inter alia the steps of: (i) providing a suture construct attached to a button by swaging or cinching together ends of a suture strand woven through holes of the button to form a button/suture loop system; (ii) passing the swaged-together ends of the suture through drill holes in the first and second metatarsals; (iii) pulling the ends of the suture until the button abuts the second metatarsal; (iv) removing (by cutting, for example) the swaged together portion of the suture; (v) attaching the suture ends to another (second) button; and (vi) adjusting the first metatarsal to a correct intermetatarsal angle, and securing the first metatarsal in place by the suture-button construct and the second button.

BRIEF DESCRIPTION OF THE DRAWINGS

FIGS. 5-12 illustrate subsequent steps of a method of correcting problems associated with hallux valgus employing the suture-button construct of the present invention.

DETAILED DESCRIPTION OF THE INVENTION

Figure 1:
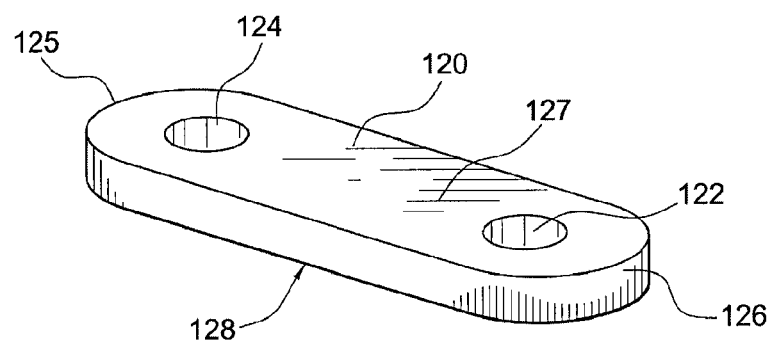
FIG. 1 illustrates a schematic perspective view of an oblong button which forms part of the suture-button construct of the present invention.

FIG. 1 illustrates button 120 used in corrective surgery for hallux valgus. Button 120 is an oblong shaped plate with chamfered or rounded corners and edges. Button 120 has a length that extends from proximal end 125 to distal end 126. Button 120 further has a width that is shorter than the length. Button 120 also has front face 127 and back face 128, wherein the distance between the front and back face 127, 128 is smaller than the width of button 120. In another embodiment, the distance between front and back face 127, 128 is greater than the width of button 120.

Button 120 further includes holes 122 and 124 that extend from front face 127 to back face 128. Hole 122 is located near distal end 126. Hole 124 is located near proximal end 125. Holes 122 and 124 are of sufficient diameter to allow suture 110 to pass through, but not so large as to severally compromise the integrity and strength of button 120.

Figure 2:
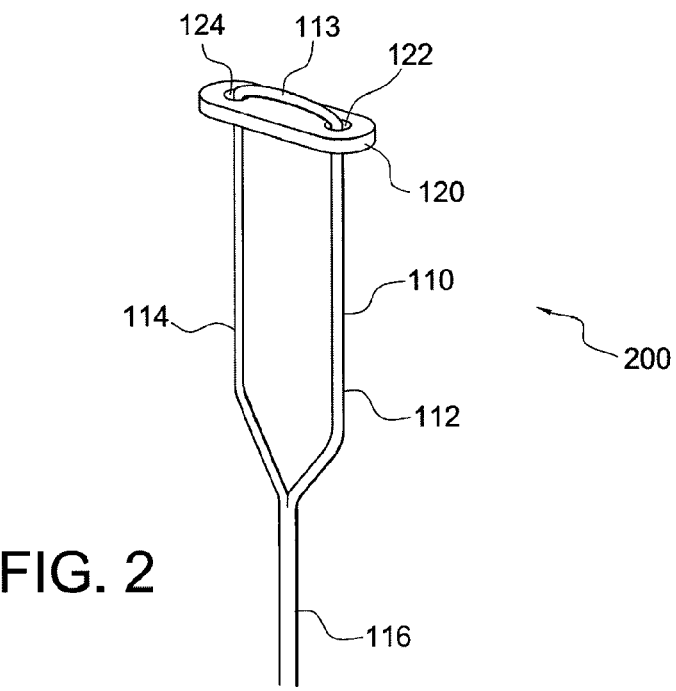
FIG. 2 illustrates an embodiment of a suture-button construct of the present invention.

FIG. 2 illustrates suture-button construct 200 (attachment 200) that includes a suture 110 and a button 120. Suture 110 is a threadlike material that is commonly employed in surgery to hold tissue or bone together. In this embodiment, suture 110 is #2 FiberWire® from Arthrex. In other embodiments, different types of sutures and different sizes of sutures may be used.

As shown in FIG. 2, suture 110 passes through first hole 122 of button 120 and through second hole 124. As a result, suture 110 includes first leg 112 that passes through hole 122 and extends away from back face 128 and second leg 114 that passes through hole 124 and also extends away from back face 128. Suture 110 also includes connecting leg 113 that extends between first hole 122 and second hole 124 along front face 127 of button 120.

In suture-button construct 200, first leg 112 and second leg 114 of suture 110 are swaged together to form combined leg 116 (single tail 116) of suture 110. As a result, part of suture 110 is formed into a continuous, uninterrupted loop with the loop portion of suture 110 passing through holes 122 and 124 of button 120.

A method of conducting surgery to reduce the intermetatarsal angle by fixating the first metatarsal using suture-button construct 200 (attachment 200) is now described. Preparation for an exemplary surgical technique relies upon radiographic film, surgical templates, and trial implants to determine and select the appropriate combination of suture 110 and button 120 that meets the patient's anatomical requirements.

Figure 3:
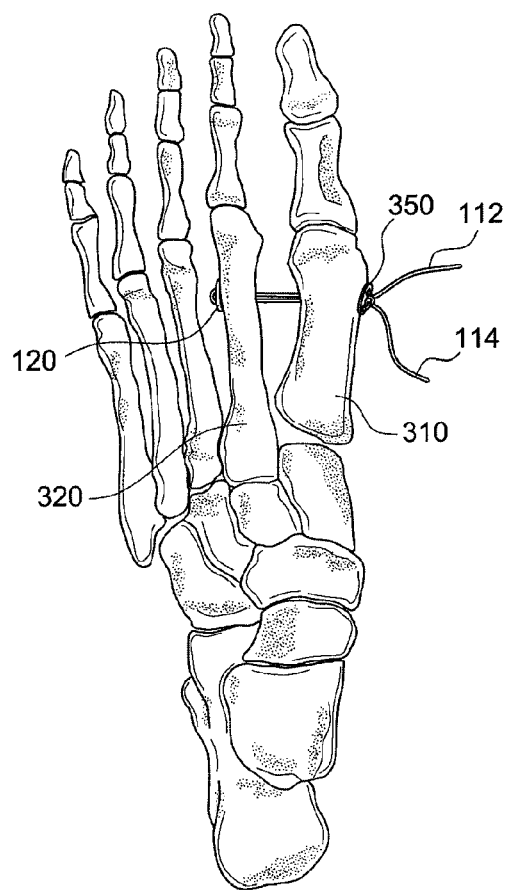
FIG. 3 illustrates a schematic view of a patient's foot with a hallux valgus repair according to a first embodiment of the present invention (and illustrating the suture-button construct of the present invention and another button, one each against the first and second metatarsals).
Figure 4:
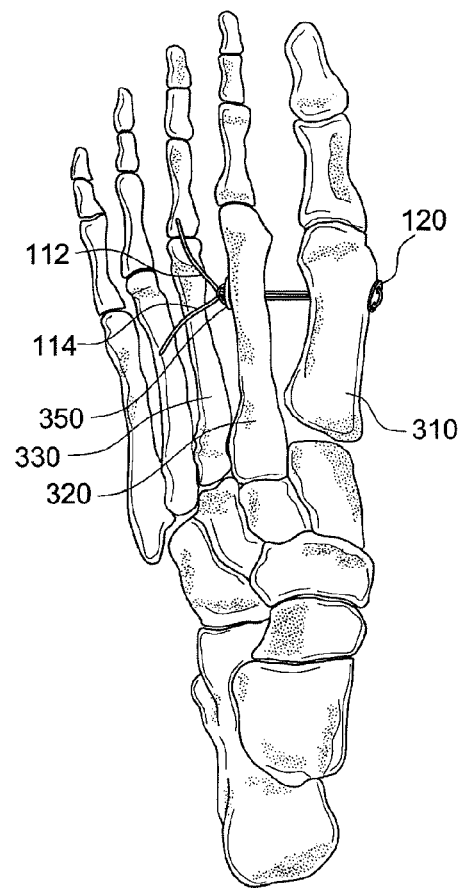
FIG. 4 illustrates a schematic view of a patient's foot with a hallux valgus repair according to a second embodiment of the present invention.

FIGS. 3 and 4 illustrate final hallux valgus repairs with the suture-button construct 200 (attachment 200) of the present invention. Referring to FIG. 3, in a first embodiment of the invention, a surgeon drills a hole using a suture passing K-wire through first metatarsal 310 and second metatarsal 320, drilling from second metatarsal 320 to first metatarsal 310. Suture-button construct 200 is loaded on the K-wire with combined leg 116 of suture 110 attached to the K-wire. Combined leg 116 of suture 110 is shuttled completely through the holes in first metatarsal 310 and second metatarsal 320 by the K-wire. Suture 110 then continues to be shuttled through until button 120 of attachment 200 rests against the lateral cortex of second metatarsal 320.

With button 120 resting against second metatarsal 320, first leg 112 and second leg 114 of suture 110 will have been shuttled through the holes in first metatarsal 310 and second metatarsal 320. First and second legs 112, 114 of suture 110 are then cut from combined leg 116, leaving first and second legs 112, 114 protruding from the hole in first metatarsal 310.

A second button 350 (for example, a round or oblong button 350) is then placed over first and second legs 112, 114 protruding from the hole in first metatarsal 310. First and second legs 112, 114 of suture 110 should be of sufficient length to extend through both the first and second metatarsals 310, 320 and allow for the surgeon to comfortable tie first and second legs 112, 114 over the top of second button 350. The surgeon then adjusts first metatarsal 310 to achieve a proper intermetatarsal angle. First metatarsal is secured in place by tying down second button 350 in standard fashion as shown in FIG. 3. In this manner, suture-button construct 200 in combination with second button 350 secures first metatarsal 310 at a proper intermetatarsal angle.

In an alternative embodiment, a similar method is used but in reverse order. In this embodiment, with the final step shown in FIG. 4, a surgeon drills a hole using a suture passing K-wire (in a method similar to the one described above), but drilling from first metatarsal 310 to second metatarsal 320. Suture-button construct 200 is loaded on the K-wire and combined leg 116 of suture 110 is shuttled through the holes in first metatarsal 310 and second metatarsal 320 by the K-wire. Suture 110 is shuttled through the holes in first metatarsal 310 and second metatarsal 320 until button 120 rests against the medial cortex of first metatarsal 310. First and second legs 112, 114 of suture 110 are cut from combined leg 116. First metatarsal 310 is correctly positioned and second button 350 is placed over first and second legs 112, 114 and tied down in standard fashion between second metatarsal 320 and third metatarsal 330 to secure first metatarsal 310.

FIGS. 5-12 illustrate in detail the steps of a method of correcting problems associated with hallux valgus employing the suture-button construct 200 of the present invention.

Figure 5:
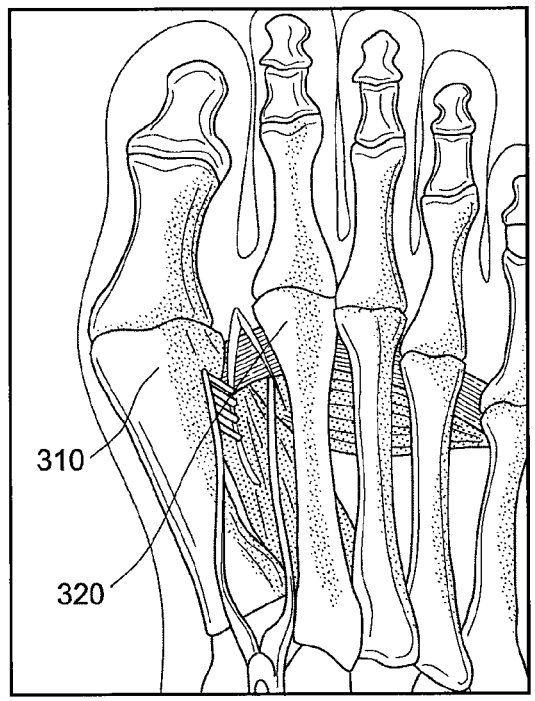

FIG. 5: For the distal approach, the first interspace release is performed through the incision made between the distal first and second metatarsals 310, 320. A dorsal medial and medial incision can also be used with appropriate distraction of soft tissues.

Figure 6:
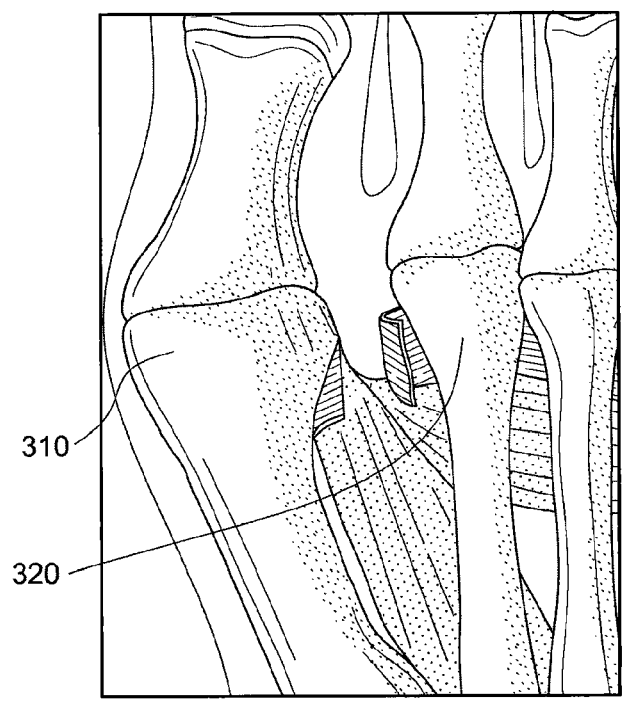

FIG. 6: To realign the fibular sesamoid, the adductor tendon is detached from both the base of the proximal phalanx and the fibular sesamoid. The deep intermetatarsal ligament and lateral capsule are released. Any sesamoid adhesions to the intermetatarsal ligament are freed.

Figure 7:
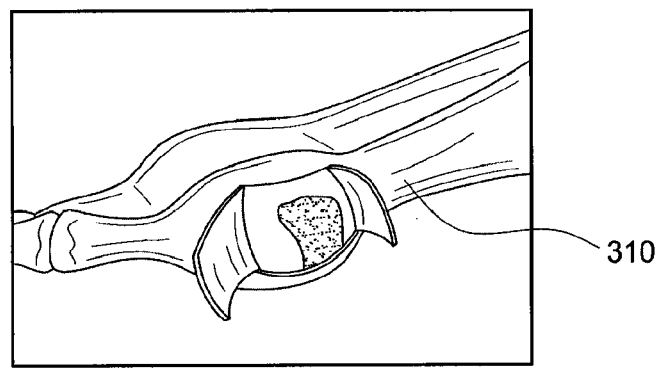

FIG. 7: The medial capsule is incised, exposing the entire medial eminence. The medial eminence is removed, preserving the sesamoid groove on the plantar aspect of the first metatarsal 310.

Figure 8A:
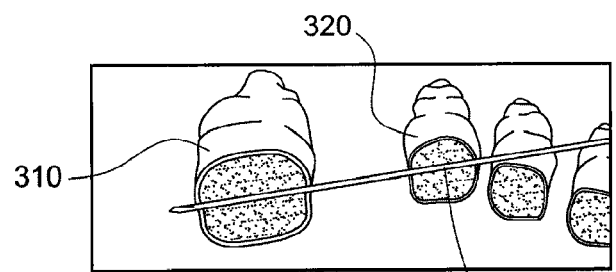
Figure 8:
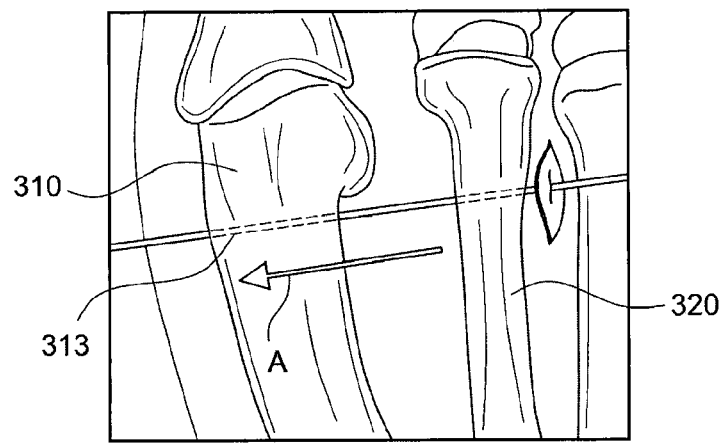

FIG. 8: The second lateral metatarsal 320 is exposed for placement of the construct 200 of the present invention. The first metatarsal 310 is reduced with provisional fixation to the second metatarsal 320. A C-arm is used to assure proper placement of a suture passing instrument 313 (for example, a 1.1 mm tapered Suture Passing K-wire 313) at the center of the second metatarsal shaft, about 2-3 mm proximal to the neck of the second metatarsal 320. The second metatarsal 320 is elevated and exposed with an elevator (for example, a Freer Elevator) and a small rake retractor (soft tissue) prior to K-wire insertion. The suture passing K-wire 313 is passed from the second metatarsal 320 through the first metatarsal 310, in the direction of arrow A. The wire should exit just proximal to the excised medial eminence. For accurate placement of the K-wire 313, the drill angle should be modified as shown in FIG. 8(a).

Figure 9:
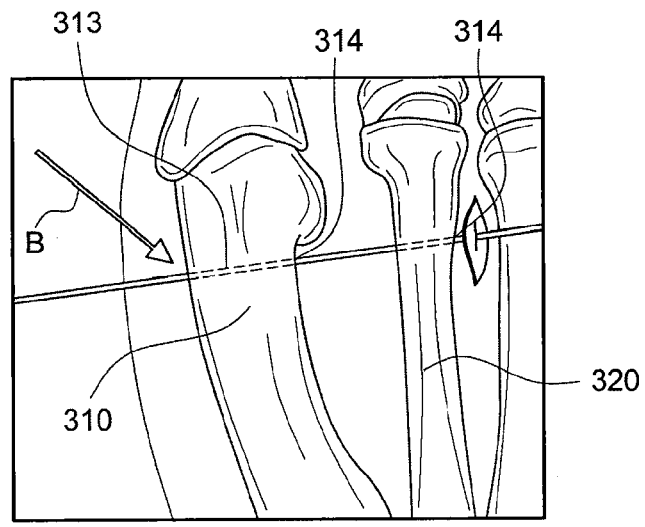

FIG. 9: With the first metatarsal 310 manually reduced, the suture passing K-wire 313 is positioned so that the tapered portions just exit the medial cortex of the first metatarsal 310 (where the pointed end of arrow B intersects the cortex of the first metatarsal 310). This will allow easy passage of the suture loop (#2 FiberWire) through the drill hole 314.

Figure 10:
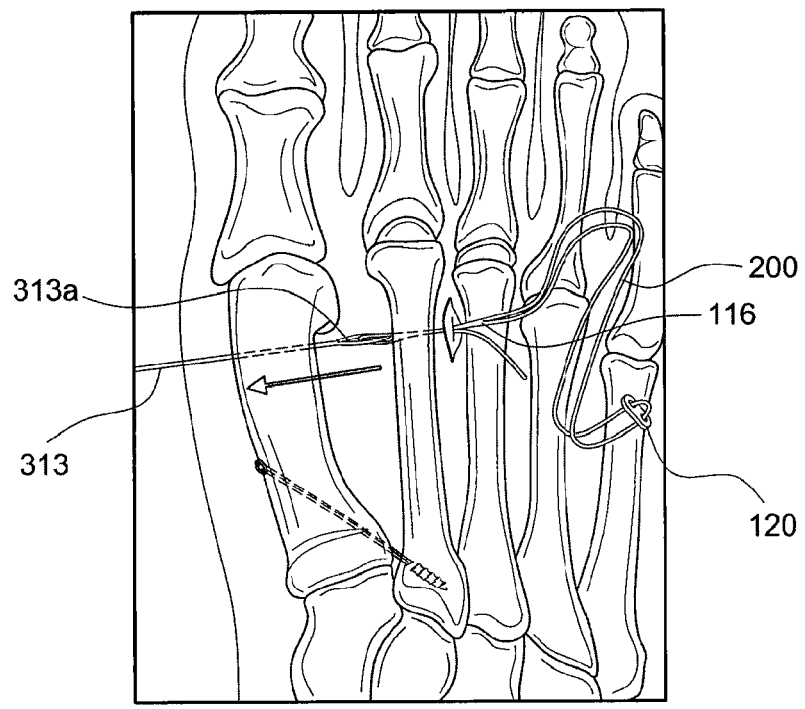

FIG. 10: Prefabricated loop 110 and leg 116 of the suture-button construct 200 is fed through the loop 313a (Nitinol loop portion 313a) of the K-wire 313. The suture passing K-wire 313 is pulled medially, passing the free end 116 of the suture construct 200 through the 1.1 mm pilot hole 314.

FIG. 11: After the suture of construct 200 has been passed from lateral to medial, the swaged portion (combined leg 116) is cut and the ends of the #2 FiberWire 112, 114 are rethreaded through opposite holes in a second button 350 (for example, an oblong button). If a round button is used, the button is threaded in the same way using opposite holes.

FIG. 12: If two constructs 200, 200a are employed for the repair, the first of two suture-button constructs 200, 200a is tied down with one knot while the second construct 200, 200a is placed about 5-7 mm proximal from the first construct. The second construct 200a is placed in a manner similar to that for the placement of construct 200 (detailed above) with same drilling and passing instructions. FIG. 12 illustrates suture-button constructs 200, 200a in combination with second buttons 350, 350a securing first metatarsal 310 at a proper intermetatarsal (IM) angle. The IM angular correction on the C-arm is checked prior to the final tightening, preferably using three knots on button 350, 350*a* for closure. FIG. 12(*a*) illustrates an X-ray depiction of the final construct of FIG. 12.

FIGS. 10(*a*)-(*d*) illustrate subsequent steps that are optional to the step illustrated in FIG. 10, i.e., instead of positioning the suture knots on the medial side of the first metatarsal 310, the knot(s) are placed lateral to the second metatarsal 320, as detailed below.

Figure 10A:
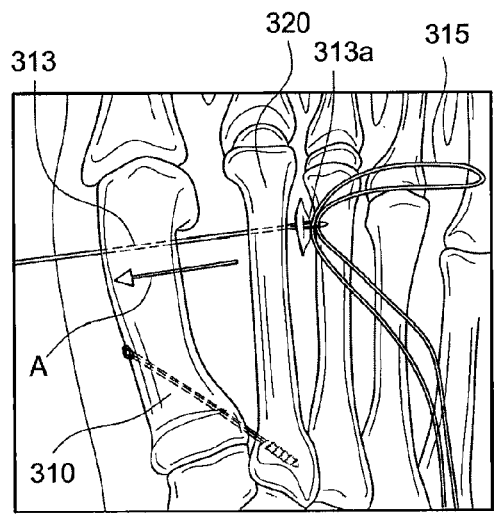

FIG. 10*a*: One limb of a passing suture 315 (for example, a 2-0 FiberWire suture 315) is passed from lateral to medial through the distal hole using the suture passing K-wire 313 with Nitinol loop 313*a* (in the direction of arrow A).

Figure 10B:
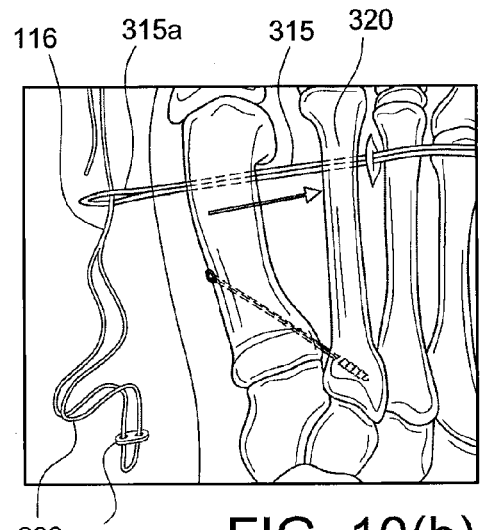

FIG. 10*b*: Making sure to hold onto the free ends of the suture 315 lateral to the second metatarsal 320, the suture passing K-wire 313 is removed. The free end 116 of suture-button construct 200 is threaded through closed end 315*a* of the passing suture 315. The construct 200 is pulled from medial to lateral back through the hole. The loop 315*a* will act as a suture shuttle, pulling the suture-button construct 200 from medial to lateral.

Figure 10C:
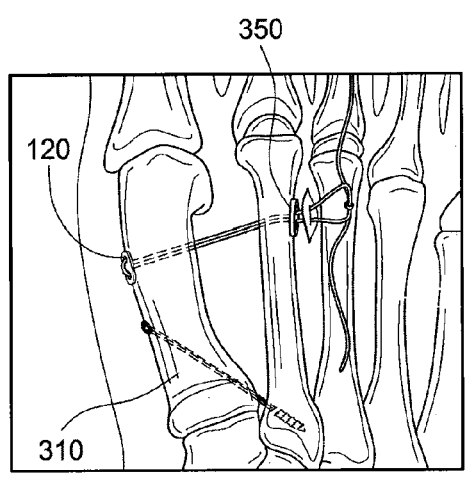

FIG. 10*c*: The passing suture 315 is removed. The construct can now be completed with a second button 350 and at least one knot (preferably three knots) lateral to the second metatarsal 320.

Figure 10D:
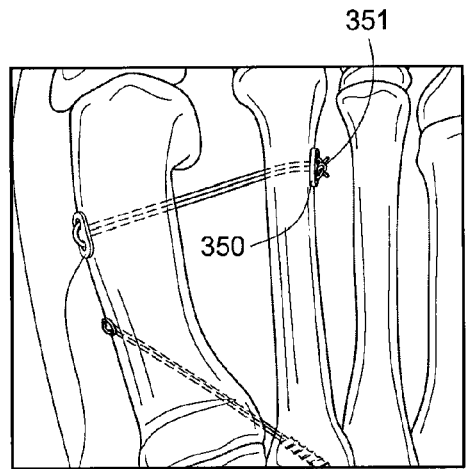

FIG. 10*d*: The final construct is illustrated with a knot 350*a* tied over the second button 350 on the lateral aspect of the second metatarsal 320.

The attachment system of the present invention has the same strength as the deconstructed Mini TightRope® from Arthrex, but reduces time in the operating room, requires only one drilled hole in lieu of multiples holes, makes the overall operation less challenging, and allows patients to return to full activities faster.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A method of bunion repair comprising:
   drilling a hole through a first metatarsal and a second metatarsal;
   providing a button/loop construct comprising a button with at least a pair of apertures, and a flexible strand loop comprising a connected to the button by passing the flexible strand through the apertures, with opposing ends of the flexible strand terminating in a combined leg;
   passing the combined leg and the loop of the button/loop construct through the hole so that the loop extends through the hole in the first and second metatarsals, and pulling the combined leg and the loop so that the combined leg and part of the loop exits the hole on a lateral side of the first metatarsal, and the button rests against a lateral cortex of the second metatarsal;
   removing the combined leg so that the opposing ends of the loop are free; and
   securing the free opposing ends to the lateral side of the first metatarsal.

2. The method of claim 1, wherein the step of securing the free opposing ends to the lateral side of the first metatarsal further comprises the step of attaching the free opposing ends to another button and securing the another button to the first metatarsal.

3. The method of claim 1, further comprising the step of attaching the combined leg of the button/loop construct to a suture passing instrument and passing the combined leg and the loop through the hole.

4. The method of claim 1, further comprising the step of manually pushing the first metatarsal and the second metatarsal together to correct intermetatarsal angular deformity.

5. The method of claim 1, further comprising the initial step of making a longitudinal incision over a medial aspect of a first metatarsophalangeal joint to expose a medial eminence; and removing the medial eminence.

6. The method of claim 1, performed in an opposite manner, such that the button is advanced in an opposite direction through the hole and ends up against the lateral side of the first metatarsal and the another button ends up against second metatarsal.

\* \* \* \* \*